United States Patent [19]

Ito et al.

[11] Patent Number: 4,966,856
[45] Date of Patent: Oct. 30, 1990

[54] ANALYTICAL ELEMENT AND THE ANALYTICAL METHOD USING THE ELEMENT

[75] Inventors: Tsukasa Ito, Musashino; Satoshi Kawakatsu, Hachioji; Akira Onishi, Hino; Masayo Takekoshi, Sagamihara, all of Japan

[73] Assignee: Konishiroku Photo Industry Co., Ltd., Tokyo, Japan

[21] Appl. No.: 110,096

[22] Filed: Oct. 15, 1987

Related U.S. Application Data

[63] Continuation of Ser. No. 874,504, Jun. 16, 1986, abandoned.

[30] Foreign Application Priority Data

Jun. 19, 1985 [JP] Japan ................ 60-131955

[51] Int. Cl.⁵ .......................................... G01N 31/22
[52] U.S. Cl. ................................. 436/170; 422/56; 422/57; 422/58; 435/4; 435/7; 435/28; 435/805; 436/172; 436/804; 436/805
[58] Field of Search ................. 422/56, 57, 58; 435/805, 4, 7, 28; 436/170, 804, 805, 172

[56] References Cited

U.S. PATENT DOCUMENTS

| | | | |
|---|---|---|---|
| Re. 30,267 | 5/1980 | Bruschi | 436/170 |
| 3,723,064 | 3/1973 | Liotta | 422/57 X |
| 3,901,657 | 8/1975 | Lightfoot | 422/58 X |
| 3,979,509 | 9/1976 | Giaever | 422/58 X |
| 3,992,158 | 11/1976 | Przybylowicz et al. | 422/57 |
| 3,996,345 | 12/1976 | Ullman, et al. | 436/800 X |
| 4,144,306 | 3/1979 | Figueras | 436/170 X |
| 4,224,304 | 9/1980 | Sawai et al. | 422/58 X |
| 4,255,384 | 3/1981 | Kitajima et al. | 422/58 X |
| 4,258,001 | 3/1981 | Pierce et al. | 422/56 |
| 4,264,327 | 4/1981 | Blum | 422/81 X |
| 4,294,817 | 10/1981 | Burgett et al. | 422/58 X |
| 4,317,810 | 3/1982 | Halbert et al. | 422/58 X |
| 4,587,099 | 5/1986 | Rothe et al. | 422/58 X |
| 4,587,102 | 5/1986 | Nagatomo et al. | |
| 4,613,567 | 9/1986 | Yasoshima et al. | 422/58 X |
| 4,806,311 | 2/1989 | Greenquist | 422/56 |

Primary Examiner—Michael S. Marcus
Assistant Examiner—Jill Johnston
Attorney, Agent, or Firm—Frishauf, Holtz, Goodman & Woodward

[57] ABSTRACT

An analytical element and method using the element for measuring a specific component in a fluid sample such as blood, serum, plasma, urine, sweat etc. The fluid sample is applied on the element with a labeled-material formed by binding the specific component or the analogue of it with a labeling material causing a signal. The element comprises a reaction layer and an absorption layer. The reaction layer contains a material which is capable of specifically binding with the component to be measured and the absorption layer contains a material which capable of binding with the labeled material and decreasing a signal caused by the labeling material. A strength of the signal caused labeled-material in the reaction layer is determined to measure the specific component.

18 Claims, 1 Drawing Sheet

ANALYTICAL ELEMENT AND THE ANALYTICAL METHOD USING THE ELEMENT

This application is a continuation of application Ser. No. 874,504, filed June 16, 1986 now abandoned.

BACKGROUND OF THE INVENTION

The present invention relates to an analytical element and a method for use in trace analysis of a fluid sample, and more particularly to an analytical element for use in the analysis of a specific microconstituent of a biological fluid sample.

Various analytical methods have been developed as the method for detecting microconstituents contained in biological fluid samples. Such analytical methods are based basically on the principle of immune reactions. Various measuring methods have been developed to date as ones using the above principle, and among these the immunity measuring method is known as the best accurate one.

As the immunity measuring method, the radiation immunity measuring method has been extensively used since when Berson and Yallow succeeded in measuring the insulin in a serum by using bovine insulin and the antiinsulin antibody in the serum of a diabetic labeled with radioactive iodide.

Since then, various materials other than radioactive isotopes as the labeled compound have been developed so far. Such various other compounds include, for example, enzymes, enzyme substrates, coenzymes, enzyme inhibitors, bacteriophages, circulation reactants, metals and ogranic-metallic complexes, organic prosthetic groups, chemical emission reactants, fluorescent moleculars, etc.

One of the important technical problems on the above immunity measuring method is the separation (hereinafter abbreviated to B/F separation) between the combined material (hereinafter abbreviated to B) and uncombined material (hereinafter abbreviated to F).

In order to solve problems in the immunity measuring method, various methods have been hitherto developed as disclosed in. e.g.. Japanese Patent Publication Open to Public Inspection (hereinafter referred to as Japanese Patent O.P.I. Publication) Nos. 38619/1978, 79024/1983, 90859/1980, 67860/1982, 200862/1982, 18167/1983, 77356/1984 and 170768/1984.

These methods, however, are disadvantageous in respect that, in these methods, the B/F separation is inadequate; there are questions in the signal's reliability because of many noises; measurable materials are limited to low-molecular materials only; and the like.

Problems which the Invention Intends to Solve

On the other hand, in wet chemistry, those immunity measuring methods by the competing process using stationary phases have been developed as disclosed in, e.g.. Japanese Patent O.P.I. Publication Nos. 209994/1983 and 202064/1984. In these methods, however, the entire enzyme's activity is measured without distinguishing both stationary phases, so that background and noise problems occur, which make it difficult to obtain any satisfactory results of the sensitivity, accuracy and reproducibility.

On the other hand, in dry chemistry, those immunity measuring methods using a second antibody have been developed as disclosed in Japanese Patent O.P.I. Publication Nos. 82766/1982 and 82767/1982. These methods, however, have room for improvement in respect that the procedure thereof is troublesome, and techniques for well reproducible development is needed, and so forth. Further, the invention of Japanese Patent O.P.I. publication No. 34155/1984 discloses a method which uses an uncombined compound-holding sheet. However, even this method, if the measurement is attempted to be made with both reaction sheet and uncombined compound-holding sheet being kept in contact with each other, causes the aforementioned problem, and separating both sheets at the time of the measurement is laborious, which will be a barrier particularly to the automation of the measurement.

SUMMARY OF THE INVENTION

The present invention has been made in order to improve the aforementioned disadvantages of the prior art.

It is therefore an object of the present invention to provide an analytical element for use in making a quantitative analysis of the specific component of a fluid sample, which is capable of effecting a positive B/F separation thereinside with little background and noise and which is excellent in the sensitivity, accuracy and reproducibility.

The objects of the invention can be accomplished with an analytical element for measuring a specific component (X) in a fluid sample by means of competing reactions between a reaction of component (X) with a material (R) which is capable of being specifically bound to component (X) or an analogue (AX) of component (X). and a reaction of labeled-substance (LX), which is formed from binding specific component (X) or the analogue thereof (AX) with a labeling material (L). with material (R), the analytical element comprising, the first layer containing material (R) (hereinafter abridged top reaction layer) and the second layer containing a material (A) which is capable of at least reducing a signal caused by labeling substance (L) in labeled-material (LX) by specifically binding with a labeling portion of labeled-material (LX) (hereinafter abridged to absorption layer), and an analytical method using the element.

DETAILED DESCRIPTION OF THE INVENTION

Figure 1:
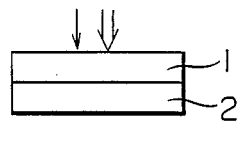
FIGS. 1 through 7 are cross-sectional schematic drawings showing examples of the analytical element of this invention.

Fluid samples usable in this invention include all forms of solutions and colloidal solutions, preferably fluid samples stemming from life, i.e., blood, blood plasma, serum, cerebrospinal fluid, saliva, amniotic fluid, milk, urine, sweat, meat juice, and the like, and particularly preferably blood and serum.

The foregoing specific component (hereinafter referred to as the component (X)) of a fluid sample measurable by this invention implies a material or a group of materials measurable with respect to the presence thereof and the amount thereof in the fluid sample, for which fluid sample a material {hereinafter referred to as substance (R)} capable of specifically combining with the component (X) is available. Examples of the component (X) include the following materials and groups of materials given in Table I:

TABLE 1

(Proteins)

| | |
|---|---|
| Albumin, | prealbumin, |
| $\alpha_1$-acid glycoprotein, | $\alpha_1$-glycoprotein, |
| tryptophan-deficient $\alpha_1$-glycoprotein, | $\alpha_1$-lipoprotein, |
| | $\alpha_1$-antitrypsin, |
| $\alpha_2$-glycoprotein, | $\alpha_2$-lipoprotein, |
| $\beta$-lipoprotein, | $\beta$-glycoprotein, |
| C-reactive protein, | fibrin-eliminated product, |
| fibrinogen, | immune globulin A, |
| immune globulin D, | immune globulin E, |
| immune globulin G, | immune globulin M, |
| haptoglobin, | hemoglobin, |
| ceruloplasmin, | cholinesterase, |
| hemopexin, | mycoglobin, |
| rheumatoid factor, | thyroxine-combined globulin, |
| transferrin, | transcortin, |
| plasminogen, | specific antibody, |
| cohesion factor, and | complementary factor. |

(Peptide hormones)

| | |
|---|---|
| Adrenocorticotropin (ACTH), | methionine- and leucine-enkephalin, |
| thyroxine, and | triiodothyronine. |

(Protein hormones)

| | |
|---|---|
| Chorionic gonadotropin, | chorionic tyrotropin, |
| glucagon, | insulin, |
| nerve growth factor, | parathyroid hormone, |
| placental lactogens, | prolactin, |
| proinsulin, and | relaxin. |

(Tissue hormones)

| | |
|---|---|
| Secretin, | gastrin, |
| angiotensins I and II, and | human placental lactogen. |

(Peptide hormones from postohypophysis)

Oxytocin, vasopressin, and releasing factors (RF):
CRF, LRF, TRF, somatotropin-RF, GHF, FSH-RF, RIF, MIF.

(Cancer cell labelers)

| | |
|---|---|
| Carcinoembryonic antigen, | gangliosides, |
| $\alpha$-fetoprotein, | basic fetoprotein, |
| pancreatic carcinoembryonic antigen, | specific $\beta_1$ glycoprotein in pregnancy, |
| TPA, | ferritin, |
| $\beta_2$-microglobulin, | myeloma protein, |
| astroprotein, | prostatic antigen, |
| squamous cell carcinoma-related antigen. | CA19-9, and |

(Microbial surface markers)

| | |
|---|---|
| Bacteria antigen, | fungi antigen, |
| helminth antigen, and | virus antigen. |

(Alkaloid medicines)

| | |
|---|---|
| Benzoylecgonine, | cocaine, |
| codeine, | dextromethorphan |
| heroin, | lysergic acid, |
| morphine, | quinidine, |
| quinine, and metabolic products of these medicines. | |

(Aminoglucoside medicines)

| | |
|---|---|
| Amicacin, | gentamicin, |
| kanamycin, | neomycin, |
| tobramycin, and metabolic products of these medicines. | |

(Antibiotics)

| | |
|---|---|
| Actinomycetin, | caromycin, |
| chloramphenicol, | chloromycetin, |
| chlorotetracycline, | erythromycin, |
| oxytetracycline, | penicillin, |
| polymyxin B, | terramycin, |
| tetracycline, | streptomycin, and |
| metabolic products of these medicines. | |

(Barbiturate medicines)

| | |
|---|---|
| Diphenyl hydantoin, | ethosuccinimide, |
| phenobarbital, | primidone, |
| secobarbital, and metabolic products of these medicines. | |

(Marijuana derivatives)

| | |
|---|---|
| Cannabinol, | tetrahydrocannabinol, and |
| metabolic products of these substances. | |

(Metabolic products)

| | |
|---|---|
| Galactose, | phenylpyruvic acid, |
| porphyrin, and | spermine. |

(Other medicines)

| | |
|---|---|
| Amitriptyline, | choline inhibitor medicine, |
| antihistaminics, | atropine, |
| butyrophenone, | caffeine, |
| carbamazepine, | chlorobromazine, |
| epinephrine, | griseofulvin, |
| imipramine, | L-DOPA, |
| lidocaine, | meperidine, |
| meprobamate, | methadone, |
| N-acetylprocainamide, | narceine, |
| nortriptyline, | oxazepam, |
| papaverine, | procainamide, |
| propranolol, | prostaglandin, |
| tegretol, | theophylline, |
| serotonin, | valproic acid, and |
| metabolic products of these compounds. | |

(Vitamins)

| | |
|---|---|
| Biotin, | folic acid, |
| thiamine, | vitamin A |
| vitamin $B_2$, | vitamin $B_6$ |
| vitamin $B_{12}$, | vitamin C, |
| vitamin D, | vitamin E, and |
| vitamin K. | |

(Steroids)

| | |
|---|---|
| Adrenocorticosteroid, | androgens, |
| bile acid, | digoxin, |
| digoxigenin, | diethylstilbestrol, |
| estrogen, and | gestagen. |

(Agricultural chemicals)

Halogenated biphenyls, phosphates, thiophosphates, and metabolic products of these chemicals.

Examples of the material (R) usable in this invention include antibodies, antigens, lectins, protein A, inhibitors against specific enzymes, and the like, according to the subject to be measured, and where the combining reaction of the specific component with the combining material is an antigen-antibody reaction is particularly preferred. The antibody to be used in this invention is not restricted by the origin thereof and may be an antiserum or ascites liquid each obtained through the immunization of a mammal or the like by administering an antigen thereto, which may be used either intact or after being refined by the prior-art methods (see Shunsuke Migida, 'Men'eki Kagaku (Immunochemistry)' pp.74–78, published by Nakayama Shoten K.K.) including the sodium sulfate precipitation method, ammonium sulfate precipitation method, gel filtration method using Sephadex gel, ion-exchange cellulose chromatography method, electrophoresis method, and the like, or alternatively may be a monoclonal antibody produced with the hybridoma obtained from the spleen cell and myeloma of a mammal (such as a mouse) immunized by an antigen.

And such antibodies may use an immunoglobulin class of IgG, IgM, IgA, IgD, and IgE, or else may be subjected to enzyme treatment to be used in the form of an active antibody fragment Fab or Fab'. Further such antibodies may be used alone or in combination of a plurality thereof. Where an antibody or antigen is used as the material (R) the measurement principle of the analytical element of this invention belongs to the immunity measuring method. The analytical element of this invention may be suitably used particularly in the immunity measuring method. The construction of the analytical element will be illustrated below by making reference to the following examples. The present invention is not restricted by the following examples, and it is apparent from what have been described above that the invention can be applied to various uses.

Those labeling material (hereinafter referred to as the material (L)) applicable to the present invention include, e.g., enzymes, enzyme substrates, materials which affect the activity of enzymes or enzyme precursors (such as enzyme inhibitors, coenzymes, prosthetic groups, materials activating enzyme precursors etc.), fluorescent materials, chemical and biological emission materials, dyes, dye precursors (such as leuco dyes), and the like. Examples representative of such materials include the following materials given in Table 2, and more preferably the enzymes and fluorescent materials disclosed in Table 2.

TABLE 2

1. Enzymes

| EC | | |
|---|---|---|
| 1.1.1.1 | alcohol dehydrogenase, | |
| 1.1.1.6 | glycerol dehydrogenase, | |
| 1.1.1.27 | lactate dehydrogenase, | |
| 1.1.1.37 | maleate dehydrogenase, | |
| 1.1.1.49 | glucose-6-phosphate dehydrogenase, | |
| 1.1.3.4 | glucose oxidase, | |
| 1.1.3.9 | galactose oxidase, | |
| 1.2.1.12 | glyceraldehyde-3-phosphate dehydrogenase, | |
| 1.2.3.2 | xanthine oxidase, | |
| | luciferase, | |
| 1.4.3.2 | L-amino acid oxidase, | |
| 1.4.3.3 | D-amino acid oxidase, | |
| 1.6.4.3 | dihydrolipoamide reductase (NAD$^+$)(diaphorase) | |
| 1.7.3.3 | urate oxidase, | |
| 1.11.1.6 | takarase, | |
| 1.11.1.7 | peroxidase, | |
| 2,7.1.1 | hexokinase, | |
| EC 2.7.1.2 | glucokinase, | |
| 2.7.1.15 | lipokinase, | |
| 2.7.1.28 | triokinase, | |
| 2.7.1.40 | pyruvate knase, | |
| 2.7.5.1 | phosphoglucomutase, | |
| 3.1.1.7 | choline estrase, | |
| 3.1.1.8 | pseudocholine esterase, | |
| 3.1.3.1 | alkaline phosphatase, | |
| 3.1.3.2 | acid phosphatase, | |
| 3.1.3.9 | glucose-6-phosphatase, | |
| 3.1.3.11 | fructose diphosphatase, | |
| 3.1.4.1 | phosphodiesterase, | |
| 3.1.4.3 | phospholipase C, | |
| 3.2.1.1 | α-amylase, | |
| 3.2.1.2 | β-amylase, | |
| 3.2.1.4 | cellulase, | |
| 3.2.1.17 | muramidase, | |
| 3.2.1.18 | neuraminidase, | |
| 3.2.1.21 | β-glycosidase, | |
| 3.2.1.23 | β-galactosidase, | |
| 3.2.1.31 | β-glucuronidase, | |
| 3.2.1.35 | hyaluronidase, | |
| 3.2.2.5 | DPN ase, | |
| 4.1.2.13 | aldolase, | |
| 4.2.1.1 | carbonic anhydrase, | |
| EC 5.3.1.1 | triosephosphate isomerase, | |
| 6.3.4.14 | biotin carboxylase, | |
| 6.4.1.1 | pyruvate carboxylase, | |
| 6.4.1.2 | acetyl-CoA carboxylase, | |
| 6.4.1 | propionyl-CoA carboxylase, and the like. | |

2. Enzyme substrates (including emission materials)
p-Nitrophenyl-β-D-galactoside,
o-nitrophenyl-β-D-galactoside,
4-methylumbelliferone-β-D-galactoside,
p-nitrophenyl phosphate,
cortisol-21-hemisuccinate umbelliferone conjugate,
luminol.
isoluminol,
N-(4-aminobutyl)-N-ethyl isoluminol hemisuccinamide,
N-(6-aminohexyl)-N-ethyl isoluminol,
N-(4-aminobutyl)-N-ethyl isoluminol,
luciferin,
acridinium phenyl carboxylate,
lophine,
pyrogallol,
gallic acid,
siloxine,
bis(2,4,6-trichlorophenyl) oxalate, and derivatives of the above compounds.

3. Enzyme inhibitors
Physositigmine,
methionine sulfoximine,
wildfirs,
blue dextran
o-dianisidine-cellulose,
o-dianisidine-dextran,
2-propinylamine,
2-chloroarylamine,
phenylglycine,
p-nitrophenylglycine,
aminoacetonitrile,
2-amino-3-hydroxypropyl-1,3'-carboxy-3'-amino-1'-propenyl-1-ether-L-2-amino-4-methoxy-trans-3-butenoic acid,
ethanolamine o-sulfate,
albizziin,
azaserine,
diazooxonorleucine,
diazooxonoanorvaline,
$\Delta^3$-7-aminocephalosporinoic acid,
mimosine,
2-amino-4-pentinic acid,
2-amino-4-chloro-4-pentenoic acid,
3,3-dichloralanine,
3,3,3-trichloroalanine,
D-cycloserine,
2-hydroxyl-3-butenoic acid,
N,N-trimethyl-2-propinylamine,
β-amino-propionitrile,
2-bromoethylamine,
3-desinoyl-N-systeamine,
2,3-decadienoyl-N-acetylsysteamine,
β-chloro-L-alanine,
L-serine-o-sulfate,
β-fluoroalanine,
L-vinylglycine,
D-vinylglycine,
propargylglycine,
gabaculine,
5-nitro-L-norvaline,
N-benzyl-N-methyl-2-propinylamine,
3-dimethylamino-1-propyne,
glycerol,
diisopropylphosphofluoride,
phenylmethanesulfonylfluoride,
crablunic acid,
allopurinol,
butylthine,
iodoacetic acid,
iodoacetoamide,
bestatin,
pyridoxal phosphate,
hydrazine and derivatives thereof,
nitrofuran and derivatives thereof,
nitrobenzene and derivatives thereof,
purine derivatives,
chelating agents,
heavy-metallic ions,
mercury compounds, and the like.

4. Coenzymes, prosthetic groups
FAD (flavin adenine dinucleotide),
FMN (flavin mononucleotide),
heme,
S-adenosylmethionine, THF (tetrahydrofolic acid),
TPP (thiamine diphosphate),
CoA (coenzyme A),
UDP-Glc (uridine diphosphate glucose),
PLP (pyridoxal phosphate),
ATP (adenosine triphosphate),
biotin,
Co I (nicotineamidoadeninedinucleotide),
Co II (nicotineamidoadeninedinucleotide phosphate),
adenosylcobalamin,
methylcobalamin,
CoM (2, 2'-dithiodiethane sulfonate), and
CoQ (ubiquinone).

5. Materials activating enzyme precursors
   Enteropeptidase,
   streptokinase,
   proteinkinase, and
   various proteases for enzyme precursors.

In addition, examples of the enzyme precursor include:
   Trypsinogen,
   chymotrypsinogen,
   procolipase,
   prophospholipase,
   prorenin,
   procarboxypeptidase A,
   procarboxypeptidase B,
   kininogen,
   proelastase,
   angiotensinogen,
   proinsulin,
   proparathyloid hormone,
   proglucagon,
   procollagen (soluble),
   agglutination factors XI, XII, XIII,
   procollagenase,
   prococoonase,
   prekallicrein,
   pepsinogen,
   plasminogen,
   fibrinogen,
   prothrombin,
   plasminogen proactivator, and
   proacrosin.

6. Fluorescent materials
   Fluorescein isothiocyanate (FITC),
   tetramethylrhodamine isothiocyanate (TRITC),
   rhodamine B isothiocyanate (RBITC),
   lisamine-rhodamine-B200 sulforyl chloride (RB200SC)
   umbelliferone,
   4-methylumbelliferone,
   fluorescein thiocarbamyl (FTC),
   fluorescein thiocarbamyl-diphenylglycine (FTC-DPG),
   tetramethylrhodamine (TMR),
   5-[(4,6-dichlorotriazine-2-yl)-amino]fluorescein,
   dimethylaminonaphthalene-5-sulfonyl chloride (DNS-Cl),
   fluoram,
   2-methoxy-2,4-diphenyl-3(2H)-furanone (MDPF),
   7-chloro-4-nitrobenzo-2-oxa-1,3-diazole (NBD-Cl),
   1-anilino-8-naphthalene-sulfonic acid (ANS),
   N-(3-pyrene)-maleimide (NPM),
   N-(7-dimethylamino-4-methyl-2-oxy-3-chloromethyl)-maleimide (DACM),
   N-(p-2-benzimidazoyl-phenyl)-maleimide (BIPM),
   anthracene isothiocyanate,
   fluoroanthylmaleimide (FAM), and
   various chelating agents containing rare earth elements.

The 'labelled material' obtained by the combination of a specific component (X) or the analogue thereof (AX) {hereinafter referred to as 'material (X')'} with a labeling material (L) {hereinafter collectively referred to as 'labelled material (IX)'} is a general term for those materials which are capable of being specifically combined similarly or equivalent to the the specific component (X), by the aforementioned material (R) capable of specifically combining with the component (X) and which are combined directly or indirectly by chemical means with the label labeling material (L) which the signal producing ability is kept maintained. In practice, such materials can be obtained by chemically combining the foregoing labeling material (L) (hereinafter simply referred to as the label) in a manner of the prior art with the specific component or a material having an antigen-determining group common to the specific component, and more particularly, can be obtained by making reference to those methods described in the 'Koso Men'eki Sokutei-Ho (Enzyme Immunity Measuring Methods)(2nd ed.)' edited by Eiji Ishikawa, Tadashi Kawai and Kiyoshi Miyai (published by Igaku Shoin in 1978) and the 'Immunoassay for Clinical Examinations—Techniques and Applications', extra edition No. 53 of the 'Rinshobyori (Clinical Pathology)' edited by the Japan Society of Clinical Pathology (1983). Methods of obtaining such materials will be illustrated by the following examples, but this invention is not limited thereto.

1. A method in which the material (X') E and enzyme are made react with a cross-linking agent such as:
   (1) 2,4,6-trichloro-1,3,5-triazine,
   (2) 4,4'-difluoro-3,3'-dinitrodiphenylsulfone,
   (3) toluene-2,4-diisocyanate,
   (4) N,N-dicyclohexylcarbodiimide,
   (5) 1-(3-dimethylaminopropyl)-3-ethylcarbodiimide,
   (6) bisdiazo-o-dianisidine,
   (7) glutaraldehyde, or the like.

2. A method in which, when at least either one of the material (X') and enzyme has a sugar chain, the sugar chain is treated with periodic acid, whereby the produced aldehyde group is made react with the amino group of an opponent material to be combined (If necessary, an additional measure may be taken which is such that, in order to prevent the formation of the undesirable linkage occurring at the time of the periodic acid treatment, the material X' or enzyme is pretreated with 1-fluoro-2,4-dinitrobenzene, or the periodic acid treatment reaction's pH is controlled to be from 4 to 5, or else the linkage of Schiff's base formed between the material E and enzyme is treated with sodium borohydride or ethanolamine or the like to be stabilized. 3. A method in which, where the material (X') and enzyme have thiol groups or produce thiol groups by reduction, etc , or are treated with an appropriate compound to thereby enable the introduction of thiol groups thereto, various cross-linking agents known as maleimide reagents are used to react with the thiol groups.

In this instance, those compounds for use in introducing the thiol group include the following examples:
   (1) anhydrous s-acetylmercaptosuccinic acid,
   (2) methyl-3-mercaptopropion imidate,
   (3) methyl-4-mercaptobutyl imidate,
   (4) 2-iminothiothiolane, (5) 3-(2'-dithiopyridyl)propionic acid N-hydroxysuccinimido ester,
(6) methyl-3-(4'-dithiopyridyl)propion imidate, and the like.

And those usable as the foregoing maleimide reagent include the following examples:
(1) N,N-o-phenylenedimaleimide,
(2) N,N-p-phenylenedimaleimide,
(3) N,N'-m-phenylenedimaleimide,
(4) N,N,-oxydimethylenedimaleimide,
(5) N-succinimidyl-N-maleimido-acetate,
(6) N-succinimidyl-4-(N-maleimido)-butyrate,
(7) N-succinimidyl-5-(N-maleimido)-heptanoate,
(8) N-succinimidyl-6-(N-maleimido)-hexanoate,
(9) N-succinimidyl-4-(N-maleimidomethyl)cyclohexane-1-caboxylate,
(10) N-succinimidyl-m-(N-maleimido)-benzoate,
(11) N-succinimidyl-p-(N-maleimidophenyl)-4-butyrate,
(12) N-sulfosuccinimidyl-4-(N-maleimidomethyl)cyclohexane-1-carboxylate,
(13) N-sulfosuccinimidyl-m-(N-maleimido)-benzoate,
(14) N-sulfosuccinimidyl-p-(N-maleimidophenyl)-4-butyrate,
(15) N-succinimidyl-4-(N-maleimidomethyl)benzene-1-carboxylate, and the like.

4. A method in which a pyridyl-disulfido group is introduced to the material (X') or enzym, and the group-introduced material (X') or enzyme is made react with the thiol group which is introduced to or originally present in an opponent compound to be combined. (The introduction of the pyridyl-disulfido group may be carried out by being treated with 3-(2'-dithiopyridyl)-propionic acid N-hydroxysuccinimidoethyl ester or methyl-3-(4'-dithiopyridyl)propion-imidate or the like. And the introduction of the thiol group may be made by using those methods as described in Paragraph 3.)

5. A method in which, where the material (X') and enzyme have thiol groups or are reduced to produce thiol groups or can have thiol groups introduced thereto by being treated with an appropriate compound, the thiol group of either one of the materials is converted into a pyridyl-sulfido group, and they are then made react with the thiol group of an opponent material to be combined. (The conversion of the thiol group into the pyridyl-sulfido group may be carried out by using 4,4'-dithiodipyridine, or the like.)

6. A method in which the amino group or thiol group present in or introduced to the material (X') or enzyme is made react with p-benzoquinoline.

7. A method in which monoiodoacetic acid N-hyroxysuccinimido ester is made react with the thiol group present in or introduced to the material (X') and enzyme.

8. A method in which the antibody to the material (X') and the antibody to the enzyme are made react with an antibody which is capable of specifically combining in common with both the antibodies.

9 A method in which either one of the material (X') and enzyme is in advance linked to avidin and the other to biotin, and then both are combined by the biotin-avidin linkage.

Of these methods the glutaraldehyde method, periodic method (Nakane method) and maleimide method are particularly suitably usable.

The reaction layer in this invention is a layer for reacting the specific component (X) of a fluid sample and the labeled material (LX) competitively with a material (R) capable of specifically reacting with the component (X), and the material (R) is required to be fixed to part of or the whole of the reaction layer. And, in order to retain the fluid sample during the reacting period of time, part of or the whole of the reaction layer requires the presence therein of a porous structure having mutual contact voids (preferably 5 $\mu$m ~500 $\mu$m in diameter) which enable the fluid sample to freely come in contact with the layer.

The preferred examples of such porous structure medium include those self-bound-type grains-combined materials as described in Japanese Patent O.P.I. Publication Nos. 101760/1982, 101761/1982 and 70163/1983, and fiber structures formed by coating those fiber-dispersed liquids as described in Japanese Patent O.P.I. Publication Nos. 125847/1982 and 197466/1982, and particularly those structures comprised of one or more materials selected from granular materials of a grain size of from 10 to 350 $\mu$m and fibers of 40 to 400 mesh.

Examples of the material to be used as such granular materials include, e.g., diatom earth, titanium dioxide, barium sulfate, zinc oxide, lead oxide, microcrystalline cellulose, silica sand, glass, silica gel, cross-linked dextran, cross-linked polyacrylamide, agarose, cross-linked agarose, chitin, chitosan, various synthetic resins (such as polystyrene), and in addition, other self-bound-type grains comprising those compounds having the following reactive groups:

Exemplified compounds (1) Poly(styrene-co-glycidyl methacrylate) [90/10],
(2) poly(styrene-co-methyl acrylate-co-glycidyl methacrylate) [80/15/5],
(3) poly(styrene-co-n-butyl methacrylate-co-glycidyl methacrylate) [75/15/10],
(4) poly(styrene-co-vinylbenzyl chloride-co-glycidyl methacrylate) [80/10/10],
(5) poly(styrene-co-divinylbenzene-co-glycidyl acrylate) [90/2/8],
(6) poly(p-vinyltoluene-co-glycidyl methacrylate) [90/10],
(7) poly(methacrylate-co-glycidyl methacrylate) [80/20],
(8) poly(styrene-co-N,N-dimethylaminoethyl methacrylate) [95/5],
(9) poly(styrene-co-aziridylethyl methacrylate) [95/5],
(10) poly(styrene-co-methyl acrylate-co-acrolein) [90/5/5],
(11) poly(styrene-co-acrylamide) [95/5],
(12) poly(styrene-co-vinylthiol) [95/5],
(13) poly(styrene-co-methylolated acrylamide) [95/5],
(14) poly(styrene-co-t-butyl acrylate-clycidyl methacrylate) [90/5/5],
(15) poly(styrene-co-vinyl isocyanate) [95/5],
(16) poly(methyl acrylate-co-styrene-co-N-methylolacrylamide) [50/35/15],
(17) poly(styrene-co-glycidyl methacrylate-co-N,N-dimethylaminoethyl methacrylate) [90/5/5],
(18) poly(styrene-co-methacrylic acid-co-acrylamide) [95/2/3],
(19) poly(co-N-methylolacrylamide-co-methoxyethyl acrylate) [90/5/5],
(20) poly(p-vinyltoluene-co-N-methylolacrylamide-co-acrylic acid) [90/8/2],
(21) poly(methyl methacrylate-co-glycidyl methacrylate-co-t-butyl acrylate) [80/10/10],
(22) poly(styrene-co-$p$-vinylbenzyl chloride-co-acrylic acid-co-ureidoethyl acrylate) [75/10/5/10],

(23) poly(styrene-co-methacrylein-co-α-hydroxyethyl methacrylate) 90/5/5],
(24) ply(styrene-co-acrolein-co-acetacetoxyethyl methacrylate) [85/5/10],
(25) poly(styrene-co-N,N-dimethylaminoethyl acrylate-co-vinylsulfonylethyl methacrylate) [90/5/5],
(26) poly(p-vinyltoluene-co-aminostyrene-co-vinylsulfonylethyl methacrylate) [85/10/5],
(27) poly(styrene-co-N,N-dimethylaminoethyl methacrylate) [90/10],
(28) poly(styrene-co-acrylic acid) [97/3],
(29) poly(styrene-co-acrylamide) [97/3],
(30) poly(vinyltoluene-co-t-butyl acrylate) [95/5],
(31) poly(methyl acrylate-co-methacrylamide) [95/5],
(32) poly(styrene-co-N-methylolacrylamide)[95/5],
(33) poly(p-vinylbenzyl chloride-co-N-methylolacrylamide) [96/4],
(34) poly(styrene-co-itaconic acid) [98/2],
(35) poly(styrene-co-t-butyl acrylate) [92/8],
(36) poly(methyl acrylate-co-styrene-co-acrolein) [30/65/5],
(37) poly(methyl methacrylate-co-styrene-co-2-hydroxyethyl methacrylate) [25/70/30],
(38) poly(styrene-co-vinylsulfonylethyl acrylate) [80/20],
(39) poly(styrene-co-N,N-dimethylaminoethyl acrylate) [90/10],
(40) poly(styrene-co-methyl acrylate-co-acetacetoxyethyl acrylate [90/5/5], and
(41) poly(styrene-co-methacrylic acid) [95/5].

Shown inside the bracket which follows each of these exemplified compounds are the percentages by weight of the monomers used in the copolymerization reaction.

Alternatively, several kinds of these polymerized grains may be mixed to be used. Examples of the fiber usable in the porous reaction layer of this invention include vegetable, animal, mineral, synthesized, semi-synthesized and recycled fiber materials, such as pulp (such as powdery filter), cotton, flax, silk, wool, chitin, chitosan, cellulose esters, viscose rayon, copper-ammonia rayon, polyamides (6-nylon, 6,6-nylon, 610-nylon, etc.), polyesters (polyethylene terephthalate, etc.), polyolefins (polypropylene, vinylon, etc.), glass fiber, asbestos, and the like. These may be used in the form of a mixture.

Besides, those materials as described in Japanese Patent O.P.I. Publication Nos. 53888/1974, 90859/1980 and 67860/1982, or as familiar examples, those textiles, non-woven cloths, synthetic papers, etc., produced using alone or in a mixture hygroscopic paper, Japanese paper, filter paper, brush polymer, or glass fiber, mineral fibers (such as asbestos), vegetable fibers (cotton, flax, pulp, etc.), animal fibers (wool, silk, etc.), synthetic fibers (nylon, vinylon, polyethylene terephthalate, polypropylene, etc.), recycled fibers (rayon, cellulose esters, etc.), and the like, may be used. The material capable of specifically combining with the foregoing specific component is desirable to be immobilized in part of or the whole of the inside of the porous medium, but it is also possible to immobilize the material in another porous mediaum layer made of gelatin, acrylamide, agarose, dextran, or the like, provided adjacent to and on the opposite side to the fluid sample-adding side of the foregoing porous medium layer.

Procedure of the immobilization may be in advance applied to the foregoing granular material or fiber to thereafter form a porous reaction layer, or may also be carried out after the formation of the porous reaction layer.

The immobilization of the material (R) capable of combining specifically with the specific component (X) may be accomplished by various known methods; i.e., by the physical adsorption of the material onto the surface of the porous medium or by directly or indirectly combining both materials by chemical reaction. In this instance, it is necessary to take care not to lose the specific combinability of the material to the specific component, and those methods as described in Eiji Ishikawa. Tadashi Kawai, and Kiyoshi Miyai, the 'Koso Men'eki Sokutei-Ho (Enzyme Immunity Measuring Methods) (2nd ed.)' (published by Igaku Shoin in 1978) may be used as suitable methods for this purpose.

The immobilization of the material (R) in the porous reaction layer should be such that its specific linkage portion is retained and the material is not in the condition of being free and dissolved in the fluid sample or is dispersed in the form of insoluble matter. And for this purpose, the method for use in the dispersion of couplers used in the color photographic process, described in, e.g., the 'Shashin Kogaku no Kiso, Ginen-Hen (the fundamentals of Photographic Engineering, -Silver Halides)' (Corona Publishing Co., 1978), a method for the incorporation of such materials into a lipid bimolecular layer, and the like, may also be used.

And, after the immobilization of the material (R) in order to, if necessary, eliminate a nonspecific reaction in the immunity reaction, the reaction layer may carry a protein which does not participate in the specific reaction. Representative examples of such the protein include normal serum protains of mammals, albumin, gelatin and its decomposed products, and the like.

The absorption layer in this invention is a layer, in part of or the whole of the inside of which is immobilized a label absorbing material (hereinafter referred to as material (A)) capable of at least decreasing a signal caused by the label as a result of the specific binding with the label portion of the foregoing labeled material (LE). The 'at least decreasing a signal' herein implies:

A. where the signal brought about by the label is decreased or eliminated as a result of the specific binding of the label, and B. where the signal brought about by the label is decreased or eliminated as a result of the molecular environment of the layer wherein the label is immobilized by the specific binding.

The cases Will be illustrated by the followimg examples: An example of A is the case where, if the label is, for example, an enzyme, an enzyme inhibitor is used as the material (A) capable of specifically combining with the labeled material (LX) to thereby immobilize the labeled material and to eliminate or significantly lower the activity of the enzyme.

Suitably usable examples of the combination of the enzyme and the inhibitor include biotin enzymes (such as pyruvate carboxylase, acetyl Co-A carboxylase, propionyl-CoA carboxylase, methylmalonyl-CoA carboxylase, etc.) and avidin, peroxidase and o-dianidin-dextran, lactate oxidase and 2-hydroxyl-3-butynic acid, monoamine oxidase and N,N-trimethyl-2-propinylamine or β-aminopropionitrile, and the like. In addition, those enzyme-inhibitor combinations as described or quoted in the Journal of the American Chemical Society (J. Am. Chem. Soc.) vol. 80, p. 456 (1958), Accounts Chemical Research (Acc. Chem. Res.), vol. 9, p. 513 (1976), 'Science', vol. 185, p. 320 (1974), Kagaku Kogyo (Chemical Industry,' vol 1985 p. 21 (1985), and the like, May also be suitably used. Further, those antibodies against the enzyme, which have a nature to inhibit the activity of the enzyme when combining with the enzyme, may also be suitably used.

Another example of A is the case where, when the label is a fluorescent material, if the labeled material has a nature to have its fluorescence reduced by the combination thereof with an antibody, the antibody is used as the material to specifically combine with the labeled material to thereby immobilize the labeled material and eliminate or decrease its fluorescence. The materials given in the '6. fluorescent materials' of Table 2 may be suitably used as the fluorescent label usable for this purpose.

An example of B is the case where, when the label is an enzyme, the substrate of a competitive enzyme made in common with the excessive labeling enzyme is immobilized in the absorption layer and the antibody against the labeling enzyme also being immobilized in the same absorbing layer, the competitive enzyme preventing the color formation of a color-forming system that is for use in measuring the activity of the labeling enzyme (for instance when the labeling enzyme is a peroxidase, a catalase is correspondingly used as the competitive enzyme).

As is seen from the above examples, as the material (A) to be in advance immobilized in the absorption layer of this invention various materials may be considered according to the type of the label used, and examples of such materials include, e.g., those antibodies produced from antigens as the label, lectins whose label contains a sugar chain (such as concanavalin A), inhibitors and substrate-like materials whose label is an enzyme (such as avidin to biotin enzyme), and the like.

The binding constant of these materials to the label is desirable to be smaller than that of the immobilized material in the reaction layer to the specific component (X) of a fluid sample, but even if the binding constants of both are nearly the same or have a reverse relation, when the quantitative proportion of the materials to be immobilized in the respective layers are properly settled, the object of the absorption layer of this invention can be adequately accomplished.

In order to effectively display the effect of this invention, if necessary, a white pigment such as $TiO_2$, $BaSO_4$, mica, etc., or coloring matter comprised of water-insoluble inorganic or organic colored compound particles, or light-absorbing particles such as carbon black may be mixed into the foregoing absorption layer to thereby provide light reflectivity or light imperviousness thereto. Alternatively, as another embodiment a reflective layer or light-impervious layer containing such materials may also be provided between the foregoing reaction layer and the absorption layer. By doing so, even if there is present a slight signal caused by the label immobilized in the absorption layer, the signal can be almost interrupted to thereby significantly lower the background of the measurement.

The absorption layer of this invention, as in the case of the reaction layer of this invention, is desirable to have in part of or the whole thereof a porous structure provided with mutual contact voids enabling the layer itself to freely come in contact with a fluid sample. Such porous medium may be one selected from the group of mediums disclosed as the porous medium applicable to the foregoing reaction layer.

The analytical element of this invention is allowed to take any form as long as it is suitable for the objective analysis and no restrictions are placed upon it, but it is desirable to be in the film or sheet form from the manufacture, procedure or measurement point of view.

In order to assist the understanding of the analytical element of this invention, the present invention will be illustrated in detail below by the accompanying drawings:

FIG. 1 is a drawing showing an example of the basic structure of the analytical element of this invention, wherein 1 is a porous reaction layer, 2 is a light-reflective absorption layer, → is the sample-drop side, and is the measuring side. A specified amount of a fluid sample is taken to be mixed with a specified amount of the foregoing labeled material (LX) and this mixture is added dropwise to porous reaction layer 1. As a result of the competitive reaction of the specific component of the fluid sample and the labeled material with the material (R) immobilized in porous reaction layer 1, part of the labeled material is immobilized in porous reaction layer 1. The remaining labeled material which has not participated in the foregoing reaction combines with the label absorbing material (A) immobilized in light-reflective layer 2 thereby to be immobilized therein. At this time, the strength of a signal caused by the label of the labeled material (LX) immobilized in porous reaction layer I is measured. For example, if the label is an enzyme, an enzyme substrate and a solution containing an appropriate color-forming system are added to the element from the upper side thereof (side 1), and the element is incubated for a specified period of time and then is measured with respect to the reflection density thereof to an appropriate wavelength-having light from the upper side of the element. In this instance, the dye formed due to the immobilized enzyme does not substantially affect the measurement because the incident light hardly reaches the upper side since not only does the activity of the immobilized enzyme in 2 is lowered but 2 has a light-reflectivity. Accordingly, the reflection density has a functional relation with the amount of the immobilized label in 1, and in addition this label amount has a functional relation with the density of the specific component which was initially present in the fluid sample. Upon this, if a calibration curve is in advance prepared using several types of fluid samples (standard samples) having known specific component (X) concentrations, the specific component's concentration in a fluid sample to be examined can be known from the reflection density.

As is apparent from the above example, the characteristic of the analytical element of this invention is such that the part of the labeled material which has not participated in the specific combining reaction in the reaction layer is separated into the absorbing layer by utilizing the specific combining reaction with the label, and further the signal produced by the label immobilized in the absorbing layer is eliminated or decreased. And by, if necessary, giving light reflectivity or light imperviousness to the absorption layer or providing additionally a reflective layer or light-impervious layer, even if the label immobilized in the absorption layer produces a slight signal, the signal can be made not obstruct the measurement of the signal brought about by the label present in the reaction layer. Consequently, the background and noise in the measurement can be significantly reduced, thereby enabling the measurement excellent in the sensitivity, accuracy and reproducibility.

The above technique is novel in the analytical system using the dry-system chemistry, and the fact that such a positive B/F separation is possible in the limited space inside an analytical element is quite an unexpected, surprising effect.

In the analytical element of this invention, the foregoing reaction layer and the absorption layer are minimum essential components, and, in order to further increase the effect of this invention, various auxiliary layers may be provided.

Figure 2:
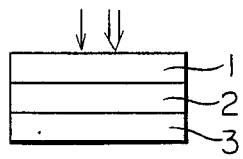

Another example of the element of this invention shown in FIG. 2 comprises a support 3 having thereon a light-reflective layer 2 and a porous reaction layer 1 in order from the support side, and this is improved for handling due to the presence of a support.

Figure 3:
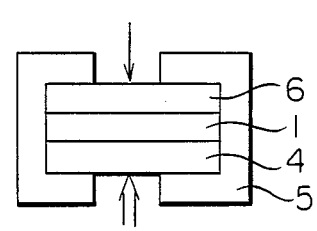

In still another embodiment of the present invention shown in FIG. 3, on a light-pervious support 4 are provided in order a porous reaction layer I and a porous light-reflective absorption layer 6, and the entire element is covered with a mount 5. When a mixture of a specified amounts of a fluid sample and a label is added dropwise through the sample inlet at top of the mount to the element, the dropped liquid becomes diffused into the porous light-reflective absorption layer and porous reaction layer. The respective reactions in the reaction layer and the absorption layer are equilibrated, making progress simultaneously. The signal caused by the label immobilized in the reaction layer may be optically measured through the light-pervious support from the measurment hole at the bottom of the mount.

No restrictions are placed on the material as the support to be used as in the above two examples, and examples of the materials include cellulose acetate, polymer materials such as polyethylene terephthalate, polycarbonate and polyvinyl compounds (such as polystyrene), etc., or glass. Further, where no light-imperviousness is needed, any one of ceramics and metals may be used, or waterproofed papers laminated with resins may also be used.

Figure 4:
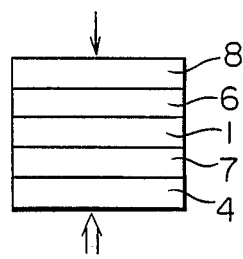

In an embodiment as shown in FIG. 4, on a light-pervious support is provided a color-forming reagent layer 7, and on the topmost of the element is provided a labeled material-containing layer 8. The labeled material-containing layer is a layer prepared by incorporating a labeled material into a porous medium (aforementioned as the medium applicable to the reaction layer) so that the labeled material concentration per unit area is constant, and when a specified amount of a fluid sample is added dropwise, a given amount of the labeled material is dissolved out to be diffused along with the sample into the reaction layer and absorbing layer. The color-forming reagent layer is a layer which is effective particularly when a signal caused by the label is brought about by the enzyme reaction and is a layer containing a hydrophilic polymer such as gelatin, polyvinyl alcohol, polyvinylpyrrolidone, agarose, sodium alginate, polyacrylamide, sodium polyacrylate, or the like, and a substrate necessary for the measurement of the enzyme activity and a color-forming reagent. The color-forming reagent layer comprises at least one hydrophilic colloid layer containing a substrate and a color-forming reagent necessary when measuring the enzyme activity.

In the analytical element of this invention, the substrate and color-forming agent may be dissolved or dispersed into a binder comprised of a hydrophilic binder to thereby form a coating liquid. Particularly for the dispersion of hydrophobic compounds various dispersion methods of the prior art such as the oil-protect dispersion method, direct dispersion method etc., which are frequently used in the photographic field, may be used.

Examples of the hydrophilic colloid applicable to the color-forming reagent layer of this invention include gelatin, gelatin derivatives such as phthalated gelatin, etc.; synthetic high-molecular materials such as polyvinyl alcohol, polyvinylpyrrolidone, polyvinylimidazole, polyacrylamide, sodium polyacrylate, etc.; polysaccharides as cellulose derivatives such as hydroxyethyl cellulose, carboxymethyl cellulose sodium salt, etc.; and the like. And the preferred among these are gelatin and gelatin derivatives such as phthalated gelatin.

The binder of the color-forming reagent layer of this invention, in order to improve the layer's physical characteristics such as the degree of swelling, solubility by heat, etc., may be substituted in part by other water-disperse high-molecular polymer; i.e. high-molecular latex. Useful examples of the high-molecular latex include those as described in, e.g., Japanese Patent Application Nos. 1931/1981 and 177596/1981. These high-molecular latexes are capable of substituting 70% maximum of the hydrophilic colloid binder, but the preferred degree of substitution is not more than 55%.

To the color-forming reagent layer may be added other additives such as, e.g., buffer, preservative, hardening agent, surface active agent, mordant, and the like, according to the purpose for which the element is used.

The thickness of the layer is from about 3 to about 50 $\mu m$. and preferably from about 5 to about 30 $\mu m$, The buffer is used for the purpose of adjusting the pH to a value suitable for the specific combining reaction, enzyme reaction, color-forming reaction, and the like. Applicable examples of the buffer include those as described in the 'Kagaku Binran Kiso-Hen (Handbook of Chemistry -Fundamentals-)' compiled by the Chemical Society of Japan (Maruzen, 1966) p. 1312-1320; N. E. Good et al, the 'Biochemistry', vol. 5, p. 476 (1966); Imamura and Saito, the 'Kagaku no Ryoiki (the Field of Chemistry)' vol. 2, p. 79 (1976); W. J. Ferguson, the 'Analytical Biochemistry' vol. 104, p. 300; and the like. Concrete examples of the buffer include borates, phosphates, carbonates, tris, barbital, glycine, Good's buffer, and the like. Any of these buffers may, if necessary, be incorporated into a layer other than the color-forming reagent layer.

The preservative is used for the purpose of stabilizing the preservability of the substrate and color-forming reagent and includes oxidation inhibitors.

In order to maintain the activities of the material capable of specifically combining with the immobilized specific component, signal modulation material and labeled material, those preservatives used for the immobilized enzyme, adsorption material of affinity chromatography, immobilized antibody, protein, enzyme, and the like, may be incorporated in the element. Applicable examples of such materials include those as described in the 'Seikagaku Jikken-Koza, Tanpakushits no Kagaku I (Biochemical Experiment Course, Chemistry of Proteins I)' compiled by the Japanese Biochemical Society (Tokyo Kagaku Dojin, K.K., 1976) p. 66-67; the 'Experiments and Applications of Affinity Chromatography' compiled by the same, p. 103-104; Japanese Patent O.P.I. Publication No. 14992/1985, and the like.

Concrete examples of such materials include gelatin. gelatin-decomposed materials, albumin, BSA, cyclodextrans, non-reducing sugars (sucrose, trehalose), polyethylene glycol, amino acids, various ions, sodium azide, and the like. These preservatives are desirable to be present in the proximity of the immobilized materials and labeled materials.

As the hardening agent those materials frequently used in the photographic field may be used, which include those as described in T. H. James, 'The Theory of the Photographic Process' p.77–87; to be concrete, aldehydes, active olefins, active esters, and the like.

Examples of the surfactant include the ones previously mentioned. Examples of the reagent to be contained in other layers include dissolving aids, blocker reagents, and the like. These additives may be added in appropriate quantities at need. The mordant is a material which concentrates the detection material for the enzyme activity measurement upon the color-forming reagent layer, or which, where the detection material is a dye, raises the absorbance coefficient, or which shifts a wavelength, and shows a strong interaction with the detection material. Cationic polymers, anionic polymers and latexes of these polymers may be used.

In this embodiment, by providing these layers only the dropping of a fluid material and incubation are enough for making the measurement.

The substrate and color-forming reagent necessary for the enzyme activity measurement differ according to labeled enzymes, and a variety of known, appropriate reagents may be used for various enzymes. These reagents contain components causing changes in spectral characteristics according to the chemical reaction catalyzed by the labeled enzyme. The above 'changes in the spectral characteristics' means not only the change in the absorbance to visible rays but also the change in the absorbance to ultraviolet and infrared rays, and also means the emission of light different from the absorption wavelength of fluorescence, the emission without absorption, and further quenching. These spectral characteristic changes include not only those directly produced by the chemical reaction catalyzed by the enzyme out also the case where the product of the enzyme reaction further causes another chemical reaction by other catalyst enzyme, thereby resulting in changes in the spectral characteristic. The substrate and color-forming reagent in this invention implies a mixture containing catalysts and enzymes other than the label, necessary for causing such spectral characteristic changes, and various substrates, coenzymes, buffers, etc., necessary for the reaction system.

A concrete construction of the above will be illustrated by taking as an example the case where the labeled enzyme is a peroxidase. In this instance, hydrogen peroxide and an appropriate reducing material are necessary as the substrate. Of these the former is volatile and it is difficult to incorporate it intact into the element, so that the hydrogen peroxide is desirable to be generated at a point of time when a fluid sample is added. This can be accomplished by incorporating, into the color-forming reagent layer in the dry state an oxidase (of the type of producing hydrogen peroxide as the reaction product) such as, e.g., glucose oxidase, amine oxidase, etc. and a substrate of the enzyme, or by incorporating either one of the oxidase and substrate into the color-forming reagent layer and the other into another layer different from the color-forming reagent layer.

On the other hand, the reducing material is desirable to have its spectral characteristic changed by being oxidized by hydrogen peroxide generated from the peroxidase. Examples of such compounds include those given in Table 3.

In addition, it has been previously described that, in the embodiment of this invention where no color-forming reagent layer is provided, when using an enzyme reaction for the detection of the label, a solution containing an enzyme substrate and a color-forming system is added dropwise to the element. In this instance and where the label is a peroxidase, those compounds disclosed in Table 3 may be suitably used as the color-forming system. In this case, it is desirable to incorporate 0.01to 30.0% hydrogen peroxide as a substrate into the solution.

Table 3

(1) o-dianidine,
(2) o-tridine or acid salts thereof,
(3) o-phenylenediamine or acid salts thereof,
(4) guaiac,
(5) adrenaline,
(6) phenolphthalein,
(7) ferrocyanides,
(8) 4-aminoantipyrin and derivatives thereof or combinations of acid salts thereof with phenol or naphthol or with derivatives thereof,
(9) aniline and derivatives thereof,
(10) monoamines such as o-toluidine, p-toluidine, etc.,
(11) diamines such as o-phenylenediamine, N.N'-dimethyl-p-phenylenediamine, N,N,-diethyl-phenylenediamine, benzidine, dianisidine, etc.,
(12) phenols such as phenol, thymol, o-. m- and p-cresol, $\alpha$-naphthol, $\beta$-naphthol, etc.,
(13) polyphenols such as catechol, guaiacol, orcinol, pyrogallol, p,p-dihydroxydiphenyl, fluoroglucinol, etc.,
(14) aromatic acids such as salicylic acid, pyrocatechic acid, gallic acid, etc.,
(15) leuco dyes such as leucomalachite green, leucophenolphthalein, etc.,
(16) coloring dyes such as 2,6-dichlorophenolindophenol, etc.,
(17) various biochemical substances such as epinophrine, flavones, tyrosine, dihydroxyphenylalanine, tryptophan, etc.,
(18) special dyes such as 2,2-azinodi(3-ethyl-6-sulfobenzothyazoline) or salts thereof, 3,3'-diaminobenzidine, etc., and
(19) other materials such as guaia gum, guaiaconic acid, potassium iodide, sodium iodide, other water-soluble iodides, and materials such as pyruvic acid.

Figure 5:
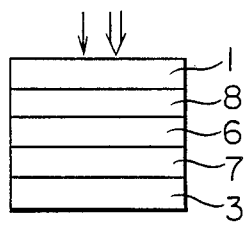

In addition, the positional relations of such color-forming reagent layer and labeled material-containing layer with the reaction layer and absorption layer may be arbitrarily settled as long as it does not obstruct the measurement of a signal in the reaction layer. FIG. 5 is a drawing showing another example of the preferred embodiment of the analytical element of this invention.

Figure 6:
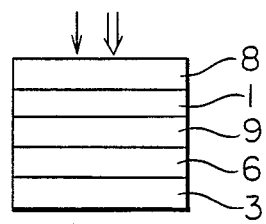

In a different embodiment of the present invention shown in FIG. 6, a timing layer 9 is provided between porous reaction layer 1 and porous light-reflective absorption layer 6. When a fluid sample is applied to the top of the element, the labeled material (LX) dissolved out from labeled material-containing layer 8 and the specific component (X) in the fluid sample competitively react with the specifically combining material (R) immobilized in the reaction layer. By the dissolution of the timing layer at a point of time when the reaction is completed, the fluid samples diffuses into the porous light-reflective absorption layer, and the labeled material which has not participated in the reaction is immobilized in the absorption layer. That the timing layer is thus used to adequately effect the competitive reaction in the reaction layer is a favorable embodiment for the purpose of increasing the sensitivity of the analytical element.

Figure 7:
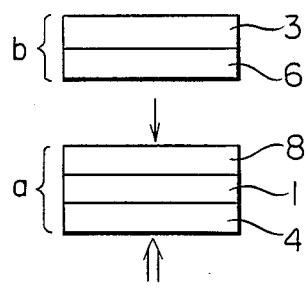

Still another embodiment of the present invention shown in FIG. 7 is also based on a similar idea. The analytical element is comprised of two elements a and b. A fluid sample is added to the top of element a to effect an adequate reaction, and after that the element is brought into contact with porous light-reflective absorption layer b, whereby the labeled-material (LX) which has not participated in the reaction is absorbed into b.

In addition, the reaction layer and the absorption layer may be peeled apart at the time of measurement. That is, the reaction layer and the absorption layer are prepared either in the integrated form or apart prior to the application of a fluidsample, and both are brought into contact with each other when adding the fluid sample to complete their reaction, and then peeled apaprt at the time of measurement.

The analytical element of this invention may have additional auxiliary layers such as a development layer which, when a fluid sample is applied to the element, assists the development of the fluid sample; a hemosegregation layer which may be required in the case where the fluid sample is blood (complete blood); an adhesion layer which may be provided at need; a protective layer; and the like. These auxiliary layers and the foregoing color-forming reagent layer, labeled material-containing layer, and timing layer may be provided either independently or in the form of layer(s) having a plurality of such functions. Positions of these layers to be provided can be easily settled according to their respective functions.

EXAMPLES

The present invention will be illustrated further in detail by the following examples. The invention, however, is not limited to and by the examples.

EXAMPLE 1

(1) Introduction of reactive group to filter:

Filter paper No. 5C (produced by Toyo Roshi K.K.) was cut into a 2 cm×2 cm square, and 11 g of it was immersed in 200 ml of a 2.5M potassium phosphate buffer solution (pH 12.1). The liquid was cooled to 5° to 10° C., and to this, with stirring, were added slowly 100 ml of cyanogen bromide solution (0.05 g/ml). After the reaction took place for 10 minutes the filter paper was taken out to be washed with distilled water cooled b ice and then with 0.1M sodium hydrogencarbonate.

(2) Preparation of reaction layer:

Zero point five milligram (in antibody protein equivalent) of the IgG fraction of a caprine anti-IgG (produced by U.S. CAPPEL LAB.) was dissolved in 20 ml of 0.1M $NaHCO_3$-0.5M NaCl solution, and to this solution were added 10 sheets of the filter paper prepared in (i), and this was shaked for three hours at room temperature. After that, the filter paper sheets were taken out to be shaked with a 1M tris-hydrochloric acid buffer solution (pH 8.0) for two hours at room temperature. The filter paper was then washed sequentially with water, 0.5M acetic acid buffer solution (pH 4.0), 0.5M $NaHCO_3$, and 0.5 mM phosphoric acid-buffered physiological salt solution (pH 7.2). This was then immersed overnight in a 50 mM tris-hydrochloric acid buffer solution containing 2% bovine serum albumin (BSA), and subsequently washed with distilled water, and, after being soaked with a slight amount of a BSA-sugar solution, was freezed to be dried.

(3) Preparation of absorption layer:

One point zero gram (in antibody protein equivalent) of the IgG fraction of a caprine antiperoxidase (produced by U.S. CAPPEL LAB.) was dissolved into 20 ml of a 0.1M $NaHCO_3$-0.5M NaCl solution, and to the solution were added 10 sheets of the filter paper prepared in (1), and this was shaked for two hours at room temperature. After that the paper sheets were taken out and immersed in a solution of 10.0 mg of a catalase (produced by U.S. SIGMA CHEM. Co.) dissolved into 20 ml of 0.1M $NaHCO_3$-0.5M NaCl solution, and further shaked for 3 hours. Subsequently the filter paper sheets were taken out to be subjected to a tris-hydrochloric acid treatment, washing and then drying in the same manner as in (2).

(4) Assembling of analytical element:

On a subbed polyethylene terephthalate film were superposedly provided one each the above prepared absorption layer and the reaction layer in the described order, whereby an analytical element was prepared.

(5) Measurement of human IgG:

0.01M sodium phosphate buffer solutions (pH 7.6) containing a human IgG (produced by U.S. CAPPEL LAB.) in various concentrations ranging from 640 $\mu g/ml$ to 0 $\mu g$ were prepared. On the other hand, a peroxidase-labeled human IgG (produced by U.S. CAPPEL LAB.) in 40 $\mu g/ml$ was dissolved into a 0.01M sodium phosphate buffer solution (pH 7.6).

10 $\mu l$ each of the respective concentrations-having human IgG liquids was added dropwise to each of the analytical element sheets, and subsequently 10 $\mu l$ of the labeled IgG solution was added dropwise to the same portion. After being kept warm for 10 minutes, to each analytical element sample were added dropwise 40 $\mu l$ of a 50 mM citric acid-disodium phosphate buffer solution (pH 5.0) containing 2.5 mg/ml of o-phenylenediamine and 0.05% $H_2O_2$. After being kept warm for 10 minutes each of the elements was measured from above with respect to the reflection density to 492 nm. The obtained results are shown in Table 4.

TABLE 4

| Human IgG concentration($\mu g/ml$) | Reflection density |
|---|---|
| 0 | 1.12 |
| 5 | 1.06 |
| 10 | 0.94 |
| 20 | 0.83 |
| 40 | 0.74 |
| 80 | 0.60 |
| 160 | 0.50 |
| 320 | 0.44 |
| 640 | 0.38 |

As a comparative example, a similar analytical element was prepared in the same manner as in the above samples except that the absorption layer prepared in 1-(3) was replaced by one in which the same filter paper is subjected to a 2% BSA treatment [see 1-(2)] alone, and the element was measured with respect to the IgG density in like manner, but there was found almost no change in the reflection density despite of the change in the human IgG concentration, thus giving no satisfactory results.

EXAMPLE 2

(1) Preparation of rabbit anti-FITC antibody:

Fifty milligrams of BSA were dissolved into 5 ml of a 0.1M sodium carbonate solution (pH 9.0), and to this solution was added a solution of 2 mg of fluorescein isothiocyanate (produced by U.S. Research Organics) dissolved into 500 μl of dimethylformamide. The mixture was stirred for 3 hours in a darkroom and then refined by a Sephadex G-25 column (manufactured by Pharmacia), and subsequently freezed to be dried.

The mixtures of this with a complete Freund's adjuvant for the first immunization only and with incomplete Freund's adjuvant, for the rest were used to immunize a rabbit.

From the obtained antiserum was separated the globulin division by the ammonium sulfate method, and after removing the antibody adsorbed to the BSA by affinity chromatography, the globulin division was dialyzed and then freezed to be dried.

(2) Introduction of reactive group into the colored filter paper:

Filter paper No. 5C (produced by Toyo Roshi K.K.) was dyed in black by a commercially available dye, and then cut into a 2 cm×2 cm square, and subsequently subjected to the same treatment as in Example 1-(1).

(3) Preparation of absorption layer:

The antibody that was obtained in Example 2-(1) was immobilized in the filter paper that was obtained in Example 2-(2) in the same manner as in Example 1-(2), and then dried.

(4) Preparation of reaction layer:

A reaction layer was prepared in the same manner as in Example 1-(2).

(5) Preparation of labeled material-containing layer:

Filter paper No. 7 (produced by Toyo Roshi K.K.) was cut into a 2 cm×2 cm square. This was immersed in a 50 mM tris-hydrochloric acid buffer solution (pH 8.0) containing 3% BSA, and, after being allowed to stand overnight, was washed with distilled water, and then dried at 35° C.

A FITC-labeled human IgG (produced by U.S. CAPPEL LAB.) in 42 μg/ml was dissolved into a 0.01M sodium phosphate buffer solution (pH 7.6), and 25 μl of this solution was added dropwise to each one of the above-prepared sheets of filter paper, and immediately freezed to be dried.

(6) Assembling of analytical element:

On a subbed polyethylene terephthalate film support were superposedly provided one each the above-prepared reaction layer, absorption layer and labeled material-containing layer in the described order, whereby an analytical element was prepared.

(7) Measurement of human IgG:

0.01M sodium phosphate buffer solutions (pH 7.6) containing the human IgG (produced by U.S. CAPPEL LAB.) in various different concentrations were prepared.

10 μl each of the various concentrations-having human IgG solutions was added dropwise to each one of the analytical elements prepared in (6), and, after being kept warm at 37° C. for 30 minutes, was measured with a fluorescent light (excitation wavelength 490 nm, fluorescent wavelength 520 nm) from underneath the support, and then the results were obtained as given in the following Table 5.

TABLE 5

| Human IgG concentration (μg/ml) | Fluorescent strength (arbitrary unit) |
| --- | --- |
| 0 | 135 |
| 5 | 122 |
| 10 | 104 |
| 20 | 89 |
| 40 | 77 |
| 80 | 66 |
| 160 | 52 |
| 320 | 47 |
| 640 | 43 |

A similar analytical element was prepared in the same manner as in the above samples except that the absorption layer prepared in 2-(3) was replaced by the same colored filter paper, and the element was measured with respect to the IgG density in like manner. The results were obtained as given in the following Table 6.

TABLE 6

| Human IgG concentration (μg/ml) | Fluorescent strength (arbitrary unit) |
| --- | --- |
| 0 | 139 |
| 5 | 130 |
| 10 | 121 |
| 20 | 113 |
| 40 | 106 |
| 80 | 100 |
| 160 | 94 |
| 320 | 89 |
| 640 | 85 |

By comparison of the results it is understood that, where the concentration of the IgG in the fluid sample is high; i.e., where the amount of the free labeled material which has not been able to react with the antihuman IgG antibody in the reaction layer, in the comparative example the signal (background) caused by the free labeled material remaining in the reaction layer is so large than the inclination of the calibration curve is very gentle, while in the analytical element of this invention the free labeled material is scavenged to the absorption layer and further loses its signal capability, so that element provides a very satisfactory calibration curve.

EXAMPLE 3

(1) Preparation of color-forming reagent layer:

On a subbed polyethylene terephthalate film support was coated in aqueous system a layer having the following composition and then dried, whereby a color-forming reagent layer was prepared.

| | |
| --- | --- |
| Glucose | 0.80 g/m² |
| o-Phenylenediamine | 0.40 g/m² |
| Citric acid | 0.16 g/m² |
| Disodium phosphate | 0.23 g/m² |
| Deionized gelatin | 16.00 g/m² |
| Bisvinylsulfonylmethyl ether | 0.02 g/m² |

(2) Preparation of absorption layer:

A reactive group was introduced to powdery filter paper D (produced by Toyo Roshi K.K.) in the same manner as in Example 1-(1), and then a similar treatment to that of Example 1-(3) took place. The powdery filter paper was used to prepare a fiber-dispersed liquid having the following composition, and this was coated on the color-forming reagent layer that was prepared in Example 3-(1), and then dried.

| Treated powdery filter paper | 5 g |
|---|---|
| Poly(styrene-co-glycidyl methacrylate)[90/10] | 0.75 g |
| Octylphenoxypolyethoxyethanol | 0.5 g |
| Xylene | 14 ml |

(3) Preparation of labeled material-containing layer:

In the same manner as in Example 2-(5) a labeled material-containing layer containg a peroxidase-labeled human IgG was prepared. This was superposed on the absorption layer that was prepared in Example 3-(2), thereby preparing an analytical element.

(4) Preparation of reaction layer:

A caprine-antihuman IgG (produced by U.S. CAPPEL LAB.), glucose oxidase and BSA were physically adsorbed to the unit surface of poly(styrene-co-n-butyl methacrylate-co-glycidyl methacylate) [75/15/10] high-molecular polymer particles of average particle size of 2 μm, and this was coated along with a 5% by weight of Triton X-100 (produced by ROHM AND HAAS Inc.) on a polyethylene terephthalate support so that its dry thickness was about 350 μm, and then dried for 30 minutes at 42° C. After the layer was formed, the layer was peeled apart from the support, and was made adhere onto the labeled material-containing layer that was prepared in Example 3-(3).

(5) Measurement of IgG:

0.01M sodium phosphate buffer solutions (pH 7.6) containing a human IgG (U.S. CAPPEL LAB.) in various concentrations were prepared. Ten μl each of the IgG solutions in various concentrations was added dropwise to each of the analytical element sheets which were prepared in (4). After being kept warm at 37° C. for 30 minutes, each element was measured from thereabove with respect to the reflection density at a wavelength of 492nm. The obtained results are shown in the following Table 7.

TABLE 7

| Human IgG concentration (μg/ml) | Reflection density |
|---|---|
| 0 | 1.38 |
| 5 | 1.27 |
| 10 | 1.12 |
| 20 | 0.96 |
| 40 | 0.78 |
| 80 | 0.60 |
| 160 | 0.39 |
| 320 | 0.20 |
| 640 | 0.11 |

EXAMPLE 4

(1) Preparation of reaction layer:

A similar particulate material to that of Example 3-(4) was coated on a subbed light-pervious polyethylene terephthalate support, and then dried.

(2) Preparation of absorption layer:

The absorption layer that was prepared in Example 2-(3) was superposed on the reaction layer that was prepared in Example 4-(1).

(3) Preparation of labeled material-containing layer:

Tha labeled material-containing layer that was prepared in Example 2-(5) was superposed on the absorption layer that was prepared in Example 4-(2).

(4) Measurement of human IgG:

When measurement was made in the same manner as in Example 2-(7), then the results was obtained as given in the following Table 8.

TABLE 8

| Human IgG concentration (μg/ml) | Fluorescent strength (arbitrary unit) |
|---|---|
| 0 | 163 |
| 5 | 150 |
| 10 | 131 |
| 20 | 113 |
| 40 | 91 |
| 80 | 62 |
| 160 | 43 |
| 320 | 19 |
| 640 | 12 |

EXAMPLE 5

(1) Preparation of absorption layer:

The reaction at pH 9 between a filter paper activated in the same manner as in Example 1-(1) and o-dianisidine took place overnight at room temperature in the dark. The filter paper was taken out, treated with 1M 1-amino-2-propanol, and washed, and then dried.

(2) Assembling of analytical element:

On the color-forming reagent layer that was prepared in Example 3-(3) were superposedly provided the absorption layer that was prepared in Example 5-(1), the labeled material-containing layer that was prepared in Example 3-(3) and the reaction layer that was prepared in Example 3-(4) in the described order, whereby an analytical element was prepared.

(3) Measurement of human IgG:

Measurement was made in the same manner as in Example 3-(5), and then the results were obtained as shown in the following Table 9.

TABLE 9

| Human IgG concentration (μg/ml) | Reflection density |
|---|---|
| 0 | 1.74 |
| 5 | 1.56 |
| 10 | 1.40 |
| 20 | 1.24 |
| 40 | 1.08 |
| 80 | 0.90 |
| 160 | 0.65 |
| 320 | 0.46 |
| 640 | 0.36 |

EFFECT OF THE INVENTION

As has been described above, the analytical element of this invention is significantly effective in respect that it is capable of making a B/F separation thereinside and of carrying out a highly sensitive, accurate and well-reproducible quantitative analysis of the specific component of a fluid sample with little background and noise.

What is claimed is:

1. An analytical element for measuring a specific component (X) in a fluid sample by means of competing reactions between a reaction of said component (X) with a material (R) which is capable of being specifically bound to said component (X) or an analogue (AX) of said component (X), and a reaction of a labeled-material (LX), which is formed from binding said specific component (X) or the analogue thereof (AX) with a labeling material (L), with said material (R), said analytical element comprising a first layer containing said material (R) immobilized therein and, a second layer containing a material (A) which is capable of at least reducing a signal caused by said labeling material (L) in said labeled-material (LX) by specifically binding with a labeling portion of said labeled-material (LX), said first and said second layers being porous.

2. The analytical element of claim 1, wherein said material (A) is contained in said second layer in an immobilized state.

3. The analytical element of claim 2, wherein said material (R) contained in said first layer is an antigen which is capable of specifically binding with an antibody.

4. The analytical element of claim 2, wherein said material (R) contained in said first layer is an antibody which is capable of specifically binding with an antigen.

5. The analytical element of claim 4, wherein said labeling material (L) is an enzyme and said material (A) contained in said second layer is an enzyme inhibitor which is capable of specifically binding with said enzyme and of reducing an activity of said enzyme.

6. The analytical element of claim 2, further comprising a layer containing said labeled-material (LX).

7. The analytical element of claim 6, further comprising a layer containing a color-forming reagent which forms a color with an enzyme.

8. The analytical element of claim 2, further comprising a layer containing the labeled-material (LX) and a color-forming reagent.

9. The analytical element of claim 2, further comprising a timing layer provided between the first layer and the second layer.

10. The analytical element of claim 1, wherein said material (R) contained in said first layer is an antigen which is capable of specifically binding with an antibody.

11. The analytical element of claim 1, wherein said material (R) contained in said first layer is an antibody which is capable of specifically binding with an antigen.

12. The analytical element of claim 1, wherein said material (A) contained in said second layer is an enzyme inhibitor which is capable of specifically binding with an enzyme (being used as the labeling material (L) and of reducing an activity of said enzyme.

13. The analytical element of claim 1, wherein said material (A) is contained in said second layer is capable of specifically binding with the labeling portion of the labeled-material (LX) and of reducing a fluorecence as a signal caused by a fluorecent substance (being used as the labeling material (L)).

14. The analytical element of claim 1, wherein said element further comprises a layer containing said labeled-material (LX).

15. The analytical element of claim 1, wherein said element further comprises a layer containing a color-forming reagent which forms a color with enzyme material.

16. The analytical element of claim 1, wherein said element further comprises a layer containing the labeled-material (LX) and a color-forming reagent.

17. The analytical element of claim 1, 14, 15 or 16, wherein said element further comprises a timing layer provided between the first layer and the second layer.

18. A method for the measurement of a specific component (X) in a fluid sample by means of competing reactions between a reaction of said component (X) with a material (R) which is capable of being specifically bound with said component (X) or an analogue of said component (AX), and a reaction of a labeled-material (LX), which is formed from binding said component (x) or the analogue thereof (Ax) with a labeling material (L), with said material (R), said method comprising, providing said fluid sample and said labeled-material (LX) into an analytical element comprising as its structural member; a first layer containing said material (R) immobilized therein and, a second layer containing a material (A) which is capable of at least reducing a signal caused by said labeling material (L) in said labeled-material (LX) by specifically binding with a labeling portion of said labeled-material (LX), said first and said second layers being porous; and measuring strength of signal caused by said labeling material (L).

* * * * *